United States Patent [19]
Dreilich et al.

[11] Patent Number: 5,315,860
[45] Date of Patent: May 31, 1994

[54] COEFFICIENT-OF-FRICTION MEASURING DEVICE, IN PARTICULAR FOR THE MEASUREMENT OF COEFFICIENTS OF FRICTION DEPENDING ON SPEED

[75] Inventors: Ludwig Dreilich, Kronberg/Ts; Karl-Friedrich Woersdoerfer, Budenheim; Thomas Egerer, Karben; Reinhold Worms, Hoexter, all of Fed. Rep. of Germany

[73] Assignee: Alfred Teves GmbH, Fed. Rep. of Germany

[21] Appl. No.: 699,857

[22] Filed: May 14, 1991

[30] Foreign Application Priority Data

May 15, 1990 [DE] Fed. Rep. of Germany ....... 4015527

[51] Int. Cl.⁵ ............................................. G01N 19/02
[52] U.S. Cl. ........................................................ 73/9
[58] Field of Search ............................ 73/862.12, 9, 10

[56] References Cited

U.S. PATENT DOCUMENTS

| | | | |
|---|---|---|---|
| 1,490,603 | 4/1924 | Elverson | 73/9 |
| 2,004,950 | 6/1935 | Jenkins | 73/862.12 |
| 3,059,464 | 10/1962 | Deane | 73/9 |
| 3,717,025 | 2/1973 | Kronenberg et al. | 73/9 |
| 4,050,290 | 9/1977 | Lönnroth | 73/9 |
| 4,051,713 | 10/1977 | Bao et al. | 73/9 |
| 4,253,326 | 3/1981 | Münnich et al. | 73/10 |
| 5,115,664 | 5/1992 | Hegde et al. | 73/9 |
| 5,212,657 | 5/1993 | Uchikawa et al. | 73/9 X |

FOREIGN PATENT DOCUMENTS

| | | |
|---|---|---|
| 820974 | 11/1951 | Fed. Rep. of Germany ... 73/862.12 |
| 3213742 | 8/1984 | Fed. Rep. of Germany . |
| 3507514 | 9/1986 | Fed. Rep. of Germany . |
| 265693 | 3/1989 | Fed. Rep. of Germany . |
| 479016 | 7/1975 | U.S.S.R. ............................ 73/862.12 |
| 531045 | 10/1976 | U.S.S.R. ............................ 73/862.12 |
| 1353417 | 5/1974 | United Kingdom . |
| 2187853 | 9/1987 | United Kingdom ............. 73/862.12 |

*Primary Examiner*—Tom Noland
*Attorney, Agent, or Firm*—Dykema Gossett

[57] ABSTRACT

A simple-design device for the measurement of coefficients of friction depending on the relative speed between a sample (8) and a brake disc (13) features a simple-design set-up and is well suited for the measurement of the changes of the coefficient of friction in the starting and in the stopping phases of the friction surface (13). The device operates by pressing the sample (8) with a defined pressing force (K1, K2) onto the friction surface (13) and simultaneously measures that force (K3) with which the samples (8) are dragged by the friction surface (13) transversely to the pressing force (K1, K2) as a function of time and speed. A brake disc can be provided as a friction surface (13). A single source of forces (K1, K2) for the pressing force can also be provided, resulting in a simple-design and sturdy structure for the device.

16 Claims, 1 Drawing Sheet

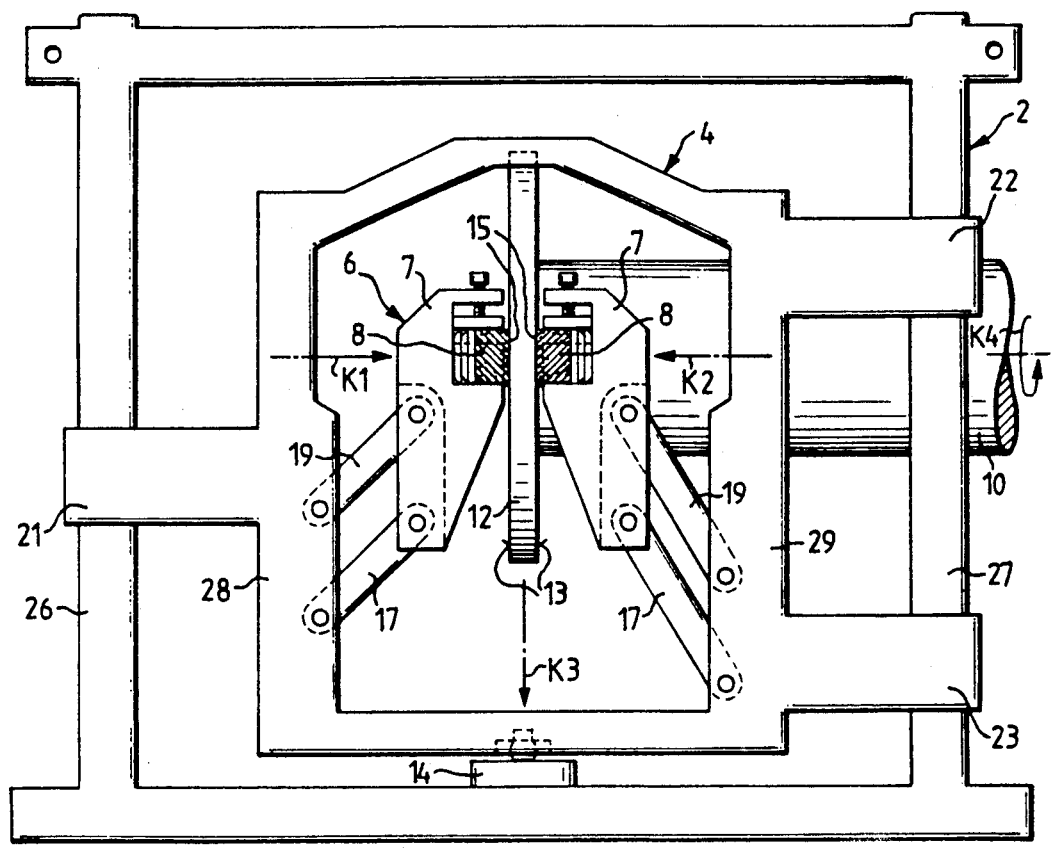

COEFFICIENT-OF-FRICTION MEASURING DEVICE, IN PARTICULAR FOR THE MEASUREMENT OF COEFFICIENTS OF FRICTION DEPENDING ON SPEED

For the research of the more precise effect of brake linings, it is necessary to find out the correlation between the coefficient of friction between the lining material and a friction surface, on one side, and different parameters, on the other side. As a matter of fact, the coefficient of friction depends not only on the speed with which the two surfaces rubbing against each other move relative to each other but also on the moisture content of the air, of the moisture content of the lining itself, on the pressing force of the linings etc. Investigations of this kind are suitable not only in view of an improvement of the braking effect but also in view of the elimination of secondary effects, such as, for example, the squealing of the brakes or the irregular rubbing of the brake lining on the brake disc.

BACKGROUND OF THE INVENTION

Investigations on the frictional behavior of objects being moved relative to each other are known, for example, from the book "PHYSIK" (Physics) by Gerthsen, published by Springer-Verlag, 1958, pages 55, 56.

BRIEF DESCRIPTION OF THE INVENTION

It is, therefore, the object of the invention to propose a device for the measurement of the frictional behavior of two bodies being moved relative to each other, which is to feature a simple design and a high degree of reliability in operation. In order to be adequate for the investigation of the behavior of brakes as to squealing and irregular rubbing, the said device should, in addition, offer the possibility to conclude on the braking behavior in the starting and stopping phases of vehicles and, thus, to roughly simulate their behavior.

In a device of the kind resulting from the general description, the object of the invention is achieved by the combination of features. That is to say, on principle the invention consists in pressing samples with a defined force against a friction surface being moved as a function of time and to measure the force so exerted on said sample in the direction of motion of said friction surface. In this context, the simplest case exists when the friction surface moves at a constant speed. Nevertheless, the invention is, in particular, suited also to measure the frictional behavior in the event of an acceleration (whether negative or positive) of the friction surface in respect of the sample, investigations being of interest in many instances in which one starts from a speed of the magnitude zero or one makes return to a speed of that magnitude. As is well known, the frictional force changes, in fact, from a fixed magnitude which is given in the presence of a constant force during the standstill of the friction surface (adhesive friction) to a frictional force decreasing as the speed increases (sliding friction), which, finally, tends to approach a limit value as the speed increases still further.

Along the lines of a further development of the inventive thought, it is recommended to apply a combination of features in order to attain a simple-design set-up of the device, as a result whereof also the space requirements are reduced.

Now, it is of importance in many instances to be given a precise indication about the frictional behavior at defined speeds so that the coefficients of friction allow to be plotted in graphs above the speed. In such cases, it is recommended that a pre-established speed, in particular a pre-established change of speed of the friction surface be imposed. In this context it is especially interesting to start from zero speed since interesting phenomena, such as the passage from the adhesive friction to the sliding friction, will, then, allow to be observed well and be recorded. In all these instances, the result is invariably the force exerted due to the friction at the different speeds as a function of the ambient parameters and/or of the force with which the sample is pressed against the friction surface.

A device of the kind mentioned above which works reliably and in an especially simple manner is obtained, in particular, when applying the combination of features in which a symmetrical distribution of forces is attained which keeps the forces acting on the device symmetrical and which, thus, takes care of a simple-design supporting of the individual components.

In accordance with one embodiment of the present invention, a load cell is used as a force measuring device whose result allows to be recorded by means of an indicating apparatus as a function of time, the speed of the friction surface existing at the different moments being pre-established as already explained above.

As a further development of the inventive thought, it is recommended to apply a combination of features including at least one retaining element positioned to be swingable on a circular arc in order to be able to support the sample holder in a simplified manner and in order to take care of a simplified absorption of the frictional forces. The aim achieved in this way is that the sample holder does not require to be movably supported in two planes but is moved on one (circular) plane only. Nevertheless, the same results as in the case of the supporting in two planes, which would appear obvious, allow, indeed, to be determined.

For a simplified structure and also, in particular, in the interest of reducing the design efforts for the supporting of the individual assemblies, the application of two retaining elements positioned symmetrically in respect to the brake disc is recommended for such an embodiment, since due to the symmetry of the acting forces the latter eliminate one another at least in one plane as far as the positioning is concerned.

For the embodiment of the swingable sample holder it will be particularly favorable to have the retaining element supported in an internal frame through trapezoidal joints, the internal frame guided in an external frame parallel to the brake disc plane and disposed vertically in respect thereto. In this way, a comparatively cheap, sturdy suspension for the samples is obtained, the lateral posts of the external frame allowing to serve simultaneously to guide the internal frame in vertical direction.

In the interest of increasing the measuring accuracy, the application of the features in which a force measuring device is disposed between the internal frame and external frame is recommended. Since the frames are as such rigid, the effect of force between the frame surfaces allows to be quite precisely. If the two surfaces of the frames which are associated with each other for the purpose of measurement are disposed parallel to each other, then it will be ensured that no transverse forces can occur in the measurement and adulterate it, provided the internal frame is guided vertically in respect of the external one.

Along the lines of a further development of the inventive thought, the combination of features wherein the internal frame is guided through three bearing points in vertical direction in respect of the external frame and positioned transversely in respect of the brake disc plane is recommended in order to prevent the clamping of the internal frame in respect of the external one and the existence of shearing forces.

The invention offers, moreover, the possibility to avoid the use of special sources of energy which supply the pressing forces insofar as the type of support of the sample holder and the existence of frictional forces are simultaneously utilized also for the generation of transverse forces. For this purpose it will be opportune to envisage the features wherein a retaining element is positioned at an angle in respect to the disc brake plane. On principle, it is the effect of this development of the inventive thought that the frictional forces are dissipated toward the internal frame at an angle in respect of the direction of motion of the friction surface of the brake disc, so that the arrow of force coming about is split up into one arrow of force determining the frictional force, which is directed vertically in the drawing, and into another one which is directed transversely in respect of the former, which forms the pressing force. It will be appreciated that this embodiment allows to do with one source of force only, which acts with the force K4 at the driving shaft. Although this system leads to self-boosting of the transverse forces as well as of the frictional forces, clear conclusions allow to be drawn on the coefficients of friction as a function of time and of speed, since the angle of action of the force conveyed from the sample holder into the internal frame and, thus, the distribution of the transverse forces K1, K2 and the force K3 measured in vertical direction are known. In this way, clear conclusions allow to be drawn on the course of the occurring transverse forces as a function of time. Indeed, the process of the device described here is, among others, suited in particular for the judgment of linings in spot-type disc brakes because the samples are comparable with pushed linings, whereas, obviously, dragged linings show a lesser tendency of squealing and irregular rubbing.

BRIEF DESCRIPTION OF THE DRAWING

One embodiment of the invention will be described in the following with reference to the accompanying drawing.

DETAILED DESCRIPTION OF THE INVENTION

In the drawing, in an external frame 2 which is provided with two vertically directed columns 26, 27 an internal frame 4 is suspended in vertical direction as viewing the drawing sliding in sliding bearings 21, 22, 23. Said internal frame 4 takes support in vertical direction on the said external frame 2 through a force measuring device 14 being configurated in the shape of a load cell, so that in the starting condition said load cell results to be loaded with the weight of said internal frame as well as of the associated components.

A portion of a circular ring-shaped friction surface 13 of a brake disc 12 which is drivable by a force K4 through a driving shaft 10 projects into an opening of an internal frame 2. On each one of two lateral posts 28, 29 of the internal frame 4 two articulated levers 17, 19 are pivoted which make catch at retaining elements 7 of a sample holder 6 on which they are pivoted, so as to constitute a trapezoidal joint. The mode of supporting is, thus, such that each of the two is retaining elements 7 swingable on a circular arc about the associated post 28, respectively 29, the two retaining elements being shifted in parallel direction only in the plane of the brake disc. As a result, friction samples 8 which are clamped in the retaining elements 7 by screw bolts maintain, with their sample surface 15, the parallel position in respect of the friction surface 13 of the brake disc 12 also in the event of a swinging motion of the levers 17, 19.

Now, while in the simplest case without the use of the swinging levers 17, 19 exclusively a pressing force being directed in the direction of the forces K1, K2 will have to be brought to bear by appropriate provisions and thereupon the force K3 be measured, the mode of operation will be the following in the embodiment described in this instance:

In the starting condition, the two retaining elements 7 are leaning against the friction surface of the brake disc 12 on account of the inclined position of the rotating levers 17, 19, and the load cell 14 will indicate a starting value K3.

Subsequently, the source of force K4 will be switched on with this process, which as a pre-established function of time drives the brake disc 12 through the driving shaft 10 with such a force that the forces of reaction of the friction are negligible. This may, for example, take place in such a way that the rotational speed of the driving shaft 10 and, thus, the speed of motion of corresponding circular sectorial ranges on the brake disc increase linearly. Due to the frictional force so originating, the entity of the forces K1 and K2 will also increase in accordance with an angular function, so that the frictional force K3 will rise and, as a consequence, also the entity of the transverse forces K1, K2.

Finally the brake disc 12 will start to race between the friction samples 8 since the effect of the force of the friction surfaces on the acceleration of the driving shaft 10 is only negligibly low. The speed of the friction surface will, finally, become that high that no further increase of the frictional forces will any longer be noticeable, so that the frictional force above the speed which still rises will approach a constant value.

By means of an indicating instrument not shown in the drawing and which records both the increasing speed of the driving shaft 10 and, thus, of the friction surface 13, on one hand, and the dependence of the frictional force K3 on the time, on the other hand, the relations of the force K3 in respect of the force K4 will allow to be recorded. As the size of the surface of attack between the sample surface 15 and the friction surface 13 does not change, also the change of the coefficient of friction will allow to be defined as a function of the speed, through the reversely calculatable pressing force K1, K2.

On this basis, so-called building-up angles allow to be calculated which substantially describe the ratio between the coefficient of adhesive friction and the coefficient of sliding friction at the beginning of the acceleration procedure of the driving shaft 10.

Besides, the building-up angle is also a measure of the change of the coefficient of friction above a constant change of speed. Now, the smaller is the change of the friction, the smaller will also be instabilities with which the lining of the sample attacks at the friction surface. In order to avoid a very short-time slip of the lining on the friction surface on account of changing coefficients of friction, one will, therefore, look for linings whose coefficients of friction change only as little as possible as the speed changes, an aspect which is valid in particular for the passage from stopping to starting, respectively from braking to stopping.

What is claimed is:

1. A device for measuring a characteristic coefficient of friction of a test sample comprising:
   guide means;
   means defining a friction surface disposed for rotation about an axis;
   sample holder means movably supported by said guide means and limited thereby to substantially linear displacement in a vertical plane parallel to said friction surface, said sample holder means operable to selectively displace said sample whereby a face thereof engages said friction surface with a pressing force directed parallel to said axis of rotation, said substantially linear displacement varying as a function of rotational speed of said friction surface at a location offset from said axis to effect a normally directed reaction force; and
   means operative to sense said reaction force and generate an output signal in response thereto.

2. A device for measuring a characteristic coefficient of friction of a test sample comprising:
   an external frame including guide means;
   an internal frame supported by said guide means and limited thereby to substantially vertical displacement;
   means defining a friction surface disposed for rotation about an axis adjacent said internal frame:
   a sample holder carried by said internal frame operable to selectively horizontally displace said test sample whereby a face thereof engages said friction surface with a pressing force which varies as a function of rotational speed of said friction surface at a location offset from said axis to effect a vertically directed reaction force;
   sensing means intermediate said internal and external frames operative to generate an output signal as a function of said reaction force.

3. A device for the measurement of a characteristic coefficient of friction of a friction sample to be tested in conjunction with a friction surface displaceable relative to the friction sample as a function of speed, wherein said friction surface is displaced as a pre-established function of time, said device comprising a sample holder operable to press said sample against said friction surface with a defined force, and a force measuring device operable to measure a resulting reaction force between the friction surface and said sample as a function of time, said sample holder comprising at least one retaining element positioned to be swingable on an arc between an engaged position with said sample in contact with said friction surface and a disengaged position with no contact between said sample and said friction surface.

4. A device as claimed in claim 3, wherein said friction surface is constituted by a brake disc driven by a driving shaft.

5. A device as claimed in claim 4, characterized in that a force which is available for acceleration of the friction surface is sufficiently high that forces decelerating the disc due to said friction surface are comparatively low and that said disc is accelerated substantially independently of the frictional forces with an acceleration which is pre-established as to time.

6. A device as claimed in anyone of claim 3, wherein said sample holder is a brake clamp including actuating ends pressed with a defined force vertically in respect of the said friction surface.

7. A device as claimed in anyone of claims 3, wherein said force measuring device is a load cell.

8. A device as claimed in claim 3, wherein said sample holder comprises a surface of the sample facing said friction surface offset parallel to a plane of said friction surface.

9. A device as claimed in claim 8, wherein said sample holder comprises two said retaining elements positioned symmetrically in respect of said friction surface.

10. A device as claimed in claim 8, wherein said force measuring device is positioned between an internal frame and an external frame in the plane of said friction surface, as a result whereof, the force of the two frames in respect of each other is measurable which results from the frictional force of the sample on said friction surface.

11. A device as claimed in claim 10, wherein said internal frame is guided through three bearing points in vertical direction in respect to said external frame and positioned transversely in respect to said brake disc plane.

12. A device as claimed in claim 8, wherein said retaining element is positioned at an angle in respect to said plane of said friction surface wherein the resulting reaction force effects an increase in said defined force.

13. A device as claimed in claim 3, wherein said sample holder is disposed within an internal frame which is disposed within an external frame.

14. A device as claimed in claim 13, wherein an end of said retaining element is connected to said internal frame.

15. A device for the measurement of a characteristic coefficient of friction of a friction sample to be tested in conjunction with a friction surface displaceable relative to the friction sample as a function of speed, wherein said friction surface is displaced as a pre-established function of time, said device comprising a sample holder operable to press said sample against said friction surface with a defined force, and a force measuring device operable to measure a resulting reaction force between the friction surface and said sample as a function of time, said sample holder comprising at least one retaining element positioned to be swingable on a circular arc, a surface of the sample facing said friction surface offset parallel to a plane of said friction surface, with said retaining element supported in an internal frame through trapezoidal joints, said internal frame guided in an external frame parallel to said friction surface plane and disposed vertically in respect thereto.

16. A device as claimed in claim 15, wherein said internal frame is guided through three bearing points in a vertical direction in respect to said external frame and positioned transversely in respect to said friction surface plane.

* * * * *